United States Patent [19]

Perlant

[11] 4,038,381
[45] July 26, 1977

[54] VACCINE FOR THE PREVENTION AND TREATMENT OF VASCULAR CONDITIONS

[76] Inventor: René Perlant, 32, Avenue de la Republique, 33 Bordeaux-Cauderan, France

[21] Appl. No.: 522,754

[22] Filed: Nov. 11, 1974

[30] Foreign Application Priority Data

Nov. 22, 1973 France ................................ 73.41544

[51] Int. Cl.$^2$ ...................... A61K 39/12; A61K 39/04
[52] U.S. Cl. ......................................... 424/89; 424/92
[58] Field of Search ..................................... 424/89, 92

[56] References Cited

U.S. PATENT DOCUMENTS 2,680,702  6/1954  Choucroun ............................ 424/92

*Primary Examiner*—Sam Rosen
*Attorney, Agent, or Firm*—Young & Thompson

[57] ABSTRACT

Vaccine for the prevention and treatment of vascular conditions, comprising a combination of a tuberculous antigen with an antiherpetic vaccine.

9 Claims, No Drawings

VACCINE FOR THE PREVENTION AND TREATMENT OF VASCULAR CONDITIONS

This invention relates to a vaccine particularly applicable to the prevention and treatment of vascular conditions.

The vaccine according to the present invention comprises a combination of a tuberculous antigen with an antiherpetic vaccine.

Useful tuberculous antigens include methylic or aqueous tuberculous antigens, and especially so-called "Antigene methylique pur Pasteur" (pure Pasteur methylic antigen).

Pure Pasteur methylic antigen is a methylic extract of tuberculous antigen containing bacillar lipoids as antigenic component.

Pure Pasteur Pasteur methylic antigen is prepared by contacting heat-killed tuberculous bacilli — from which the bacillar fats and waxes have been removed by pre-extraction with acetone — with absolute methyl alcohol, during a period of time of 10 days in an oven at 37° C.

The alcohol solvent is evaporated in vacuo. It is then replaced by sterile physiological saline solution, to give a colloidal emulsion containing about 0.20 ml antigenic component per ml.

The antiherpetic vaccine prepared by pharmaceutical laboratories, e.g. Diamant laboratory, may be used as antiherpetic vaccine.

Diamant anti-herpetic vaccine contains per ml the extract of a herpes virus culture (Herpes virus hominis) on cell cultures assaying $10^{7\pm0.5}$ DCP 50 p. 100 (cytopathogenic doses) per ml prior to inactivation and which has been completely inactivated under the controlled action of an ultraviolet radiation (the preservatives are kanamycin 0.05 mg and neomycin 0.05 mg per ml). The cytopathogenic dose 50 p. 100 or DCP 50 is the dose of viral suspension which induces lesions which are characteristic of herpes in half the tubes of cell culture. The level is calculated by the method of Reed and Muench, Am. J. Hyg. 1938, 27, 493–497.

According to an advantageous embodiment of this invention, the vaccine comprises a combination of bacillar lipoids (antigenic components of methylic tuberculous antigen) with an anti-herpetic vaccine in a ratio of about 0.02–0.20 ml antigenic components per ml of inactivated herpes virus culture assaying $10^{7\pm0.5}$ DCP 50 p. 100 prior to inactivation.

A preferred vaccine according to this invention has the following composition:

| | |
|---|---|
| Pure Pasteur methylic antigen | 0.2 ml |
| Diamant antiherpetic vaccine (per 1 ml ampoule) | 0.8 ml |

The mixed vaccine of this invention is particularly applicable to the treatment of patients suffering from coronary angina, myocardial infarction, peripheral arteritis, particularly of the lower limbs and of the brain, of polyarterial conditions and also to the prevention of these same conditions.

It should be noted that the preventive and curative properties of the mixed vaccine of this invention are different from the known properties of its components.

The vaccine according to this invention may be administered by subcutaneous, intra-arterial or intravenous injection. Preferably, however, it is administered by intradermal injection.

The above-mentioned preferred vaccine may be administered intradermally at a rate of about 0.10 to 1 ml vaccine weekly.

The vaccine may also be administered as nasal sprays or eye drops, at a rate of 0.10 ml, for example.

A clinical case report is given below for illustrative purposes.

M.F., a 66 year old male patient:

suffers from arteritis of the lower limbs limiting his walking distance to 100 m, suffers also from coronary angina requiring the daily intake of 15 Trinitrine coated tablets, complains of dizziness and of decreased attention and memory.

The patient has been under conventional treatment for a long period of time.

Under the influence of intradermal injections of the mixed vaccine consisting of methylic antigen (0.2 ml/ml) and of Diamant anti-herpetic vaccine (0.8 ml/ml) administered weekly from a dosage of 0.10 ml up to a dosage of 0.7 ml, his non-stop walking distance has increased to 500 m within three months and his Trinitrine intake has decreased to 1 coated tablet per week.

Also, dizziness has disappeared and his attention and memory have improved. He has the physiological feeling of an improved condition and he has recovered a gusto for enterprise.

The action of the mixed vaccine was investigated clinically with respect to that of its components taken individually. It was found that the action of the vaccine of this invention is superior from the standpoints of rapid action, scope of the improvement and duration of the improvement.

The invention includes also within its scope a process for the prevention and treatment of vascular conditions, comprising administering to a patient an effective amount of a combination of a tuberculous antigen with an antiherpetic vaccine.

Having now described my invention what I claim as new and desire to secure by Letters Patent is:

1. Vaccine for the prevention and treatment of vascular insufficiencies, comprising a combination of a methylic tuberculosis antigen, which is a methanol extract of killed tuberculosis bacilli after fats and waxes have been removed, and an inactivated herpes virus culture assaying $10^{7\pm0.5}$ DCP 50 p. 100 prior to inactivation, said antigen containing as antigenic component about 0.20 ml. of tuberculosis bacillar lipoids per ml. of antigen, said antigen being present in said combination in an amount of 0.02–0.20 ml. of antigen per ml. of said culture.

2. A vaccine as claimed in claim 1, in which said antigenic components are about 0.2 ml and said culture extract is about 0.8 ml.

3. A vaccine as claimed in claim 1, in which said antigenic components are Pasteur methylic antigen.

4. A vaccine as claimed in claim 1, in which said culture is Diamant antiherpetic vaccine.

5. A process for the prevention and treatment of vascular insufficiency, comprising administering to a human patient an effective amount of a vaccine as claimed in claim 1.

6. A process as claimed in claim 5, in which said vascular insufficiency is coronary angina, myocardial infarction, or peripheral arteritis.

7. A process as claimed in claim 5, in which said combination is administered by intra-dermal injection.

8. A process as claimed in claim 5, in which said antigenic components are Pasteur methylic antigen.

9. A process as claimed in claim 5, in which said culture is Diamant antiherpetic vaccine.

* * * * *